United States Patent
Mao et al.

(10) Patent No.: US 6,630,244 B1
(45) Date of Patent: Oct. 7, 2003

(54) CARBON RESISTANT SURFACE COATING

(75) Inventors: Chien-Pei Mao, Clive, IA (US); Purushothaman Kesavan, Brooklyn, NY (US); Mohan Sanduja, Flushing, NY (US); Paul Thottathil, New Hyde Park, NY (US); Carl Horowitz, Brooklyn, NY (US)

(73) Assignee: Delavan Inc., West des Moines, IA (US)

( * ) Notice: Subject to any disclaimer, the term of this patent is extended or adjusted under 35 U.S.C. 154(b) by 130 days.

(21) Appl. No.: 09/815,737

(22) Filed: Mar. 23, 2001

(51) Int. Cl.⁷ ................................................. B32B 9/04
(52) U.S. Cl. ....................................... 428/447; 428/450
(58) Field of Search ............................... 428/447, 446, 428/450

(56) References Cited

U.S. PATENT DOCUMENTS

| | | | |
|---|---|---|---|
| 5,315,822 A | 5/1994 | Edwards, III | |
| 5,336,560 A | 8/1994 | Spence et al. | |
| 5,805,973 A | * 9/1998 | Coffinberry et al. | ........ 123/668 |
| 5,833,141 A | 11/1998 | Bechtel, II et al. | |
| 6,123,273 A | 9/2000 | Loprinzo et al. | |
| 6,125,624 A | 10/2000 | Prociw | |
| 6,145,763 A | 11/2000 | Fleming et al. | |
| 6,221,498 B1 | * 4/2001 | Takahama et al. | ..... 106/287.12 |
| 6,273,348 B1 | * 8/2001 | Shouji et al. | ............. 239/585.1 |

OTHER PUBLICATIONS

Goldschmidt Chemical Corporation, Material Safety Data Sheet, Silikophen P80/20, Nov. 23, 1998, pp. 1–5.
General Electric Company; GE Silicones, Material Data Safety Sheet, SR 125 Methylphenylpolysiloxane Solution, Jun. 17, 1998, pp. 1–8.
Shell Oil Company, Material Data Safety Sheet, Methyl Ethyl Ketone, Feb. 1, 1996, pp. 2–5.
Citgo Petroleum Corporation, Material Data Safety Sheet, Xylene, Jul. 7, 1999, pp. 1–9.
Eastman Chemical Company, Material Data Safety Sheet, "Eastman" PM Acetate (propylene glycol monomethyl ether acetate), Mar. 16, 1999, pp. 2–9.
Troy Corporation, Material Data Safety Sheet, Troymax Driers (Troymax Zinc 8%), Aug. 26, 1994, pp. 1–5.
Rheox Inc., Material Data Safety Sheet, Bentone SD–2 Rheological Additive, Jul. 13, 1998, pp. 1–4.
Witco Corporation, Material Data Safety Sheet, Silquest A–1100 silane, Jan. 4, 1999, pp. 1–11.
Monomer–Polymer and Dajac Laboratories, Inc. Material Data Safety Sheet, 2,2,2–Trifluoroethyl Methacrylate, Feb. 6, 1996, pp. 1–2.

* cited by examiner

*Primary Examiner*—Robert Dawson
*Assistant Examiner*—Michael J Feely

(57) ABSTRACT

A coating formulation for application to surfaces associated with combustion, such as fuel injectors, and surfaces subjected to elevated temperatures, such as fuel supply components, to prevent the deposition at high temperatures of carbon or graphite on such surfaces, such as stainless steel and alloyed steel compositions. The coating formulation forms a thin layer of polymer coating on the surface by chemical grafting involving the use of a graft initiator to create active bonding sites, on the metal surface, for the silicone-based prepolymer to undergo polymerization on the metal surface. The bonding and polymerization are completed in a single application process without using complex equipment. The coating and process helps surfaces associated with combustion and surfaces subjected to elevated temperature reduce carbon or coke formation at temperatures up to 700° F. and thereby improves the durability and performance of those surfaces.

11 Claims, 3 Drawing Sheets

(1 of 3 Drawing Sheet(s) Filed in Color)

(A)

(B)

CARBON RESISTANT SURFACE COATING

BACKGROUND OF THE INVENTION

The present invention is related to a coating formulation, for application to mechanical devices or components having surfaces associated with or exposed to combustion and surfaces subjected to elevated temperatures by a chemical grafting technique, to prevent the deposition, at high temperatures, of carbon or coke, which can impact the performance of such devices.

In recent years, carbon deposition has become a serious problem for surfaces associated with combustion, such as fuel injectors, as well as surfaces subjected to elevated temperatures, such as turbine engines and other fuel supply components. This problem can be caused by increased fuel inlet temperatures and a higher compressor air temperatures in, e.g., gas turbines. In high-performance aircraft engines, for instance, the fuel inlet temperature might exceed 350° F. and the compressor discharge temperature could be as high as 1,600° F. Under certain operating conditions, the wetted-wall temperature quickly reaches between 400° F. and 800° F. Combined with high temperatures and slow velocities, the fuel may undergo chemical degradation, which could lead to the formation of carbon deposits within a short time. Similar deposition problems can occur in automotive applications, power generation, industrial or residential furnaces, and other similar applications.

Once carbon deposits begin to form, they contribute to a number of problems such as reduced fuel flow rate, excessive fuel pressure drop, sticking valves, blocked strainers or filters, and poor spray quality. Any one of these problems could easily affect the overall combustor performance and result in high maintenance costs.

Today's fuel injectors must often operate in a high-temperature environment without carbon formation for long hours. This requirement would be very difficult to meet without significant design improvements. Based on field experience and research studies, certain design guidelines are followed to avoid the flow or surface conditions that facilitate carbon formation. For example, the wetted-wall temperature is usually kept below 400° F., and the fuel inlet temperature must be lower than 225° F. Because fuel velocity also plays an important role in determining carbon formation, the flow rate range must be carefully examined. It has been found that carbon formation is most severe for combustors operating under soak back and steady state conditions with flow velocities ranging between 2 and 4 m/s. As fuel velocity exceeds 6 m/s, however, carbon deposition becomes less likely due to effective heat transfer and short resident times.

Despite these guidelines, engineers still have to rely on other design considerations to meet stringent requirements on injector durability and service life. These considerations include pre-stressing the fuel, using fuel additives, applying carbon-resistant coatings, providing better surface finish, adding more effective insulators, using ceramic materials, and implementing passive or active cooling. Based on a literature search and an in-depth study, the use of carbon-resistant coatings on the metal surface appears to be one of the most effective and economical means of reducing carbon formation inside fuel injector passages under adverse temperature environments.

A number of patents describe techniques for preventing the deposition of carbon onto nozzle surfaces. For example, U.S. Pat. No. 6,123,273, to Loprenzo, et al., discloses a dual fuel nozzle for inhibiting carbon deposition onto combustible surfaces in a gas turbine, in which the dual fuel nozzles produce an accelerated swirling air flow to preclude impingement of oil spray droplets onto the metal surfaces of the nozzle, and hence prevent carbon deposition thereon. U.S. Pat. No. 5,315,822, to Edwards, teaches coating fuel-wetted elements for gas turbines, where the high temperature alloys have a layer of titanium carbide, titanium nitrite, titanium boride, or mixtures thereof on them to inhibit a formation of carbon or coke. U.S. Pat. No. 5,336,560, to Spence, et al., teaches gas turbine elements which are protected from carbon deposition by the application of a coating of alumina and silica from a sol gel formulated for the purposes of creating an acceptable coating composition. U.S. Pat. No. 6,145,763 to Fleming et al. teaches coating automotive fuel injectors with a fluorine-containing amorphous hydrogenated carbon film coating to resist the formation of carbonaceous deposits. This reduction in coking and deposits improves the fuel economy and engine performance.

There are various coating techniques for improving the physical properties of stainless steel and alloy material for carbon resistance. These techniques include thermal spraying, detonation-applied refractory, chemical vapor deposition, and ion implantation. These techniques generally are complicated, expensive, and limited to specific applications.

SUMMARY OF THE INVENTION

The present invention is the discovery of a coating formulation for application to surfaces associated with combustion, such as fuel injectors, and surfaces subjected to elevated temperatures, such as fuel supply components, to prevent the deposition at high temperatures of carbon or graphite on such surfaces, such as stainless steel and alloyed steel compositions. The coating formulation forms a thin layer of polymer coating on the surface by chemical grafting involving the use of a graft initiator to create active bonding sites, on the metal surface, for the silicone-based prepolymer to undergo polymerization on the metal surface. The thin layer of polymer coating prevents the deposition at high temperatures, i.e., temperatures of from 300° F. and up to 700° F., of carbon or graphite on surfaces such as a stainless steel or stainless steel alloys. The bonding and polymerization are completed in a single application process without using complex equipment. The coating and process helps surfaces associated with combustion and surfaces subjected to elevated temperature reduce carbon or coke formation and thereby improves the durability and performance of those surfaces.

The coating is easy to apply, does not add any significant dimensions to the surface, since it is in the range of about 0.0001 to about 0.010 inch thick, but could also be about 0.0005 to about 0.003 inch thick, and cannot be easily removed. The coating process does not require expensive equipment or cause any environmental or safety hazards. The coating process can be used for parts or components with complicated configurations. Further, the coating can be used for any surfaces where the surfaces will encounter coking or carbon deposition problems, such as aircraft fuel injectors, automotive fuel injectors, fuel injectors for gas turbine power generators, and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
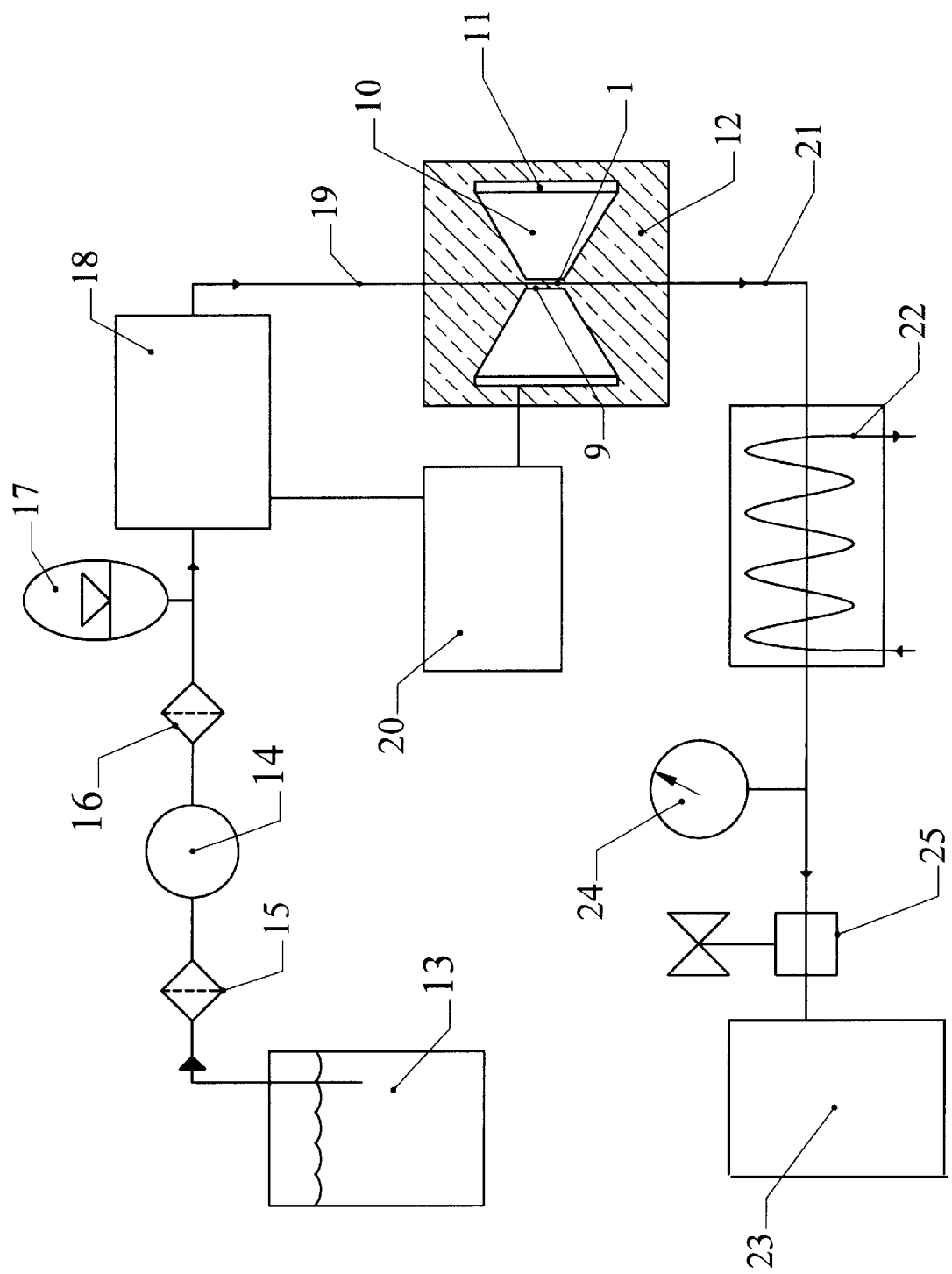
FIG. 1 is a schematic diagram of the test arrangement for the coking study.

The coating formulation of the present invention, for application to surfaces associated with combustion and surfaces subjected to elevated temperatures, to prevent the deposition at high temperatures of carbon or graphite on such surfaces, is a silicone-based prepolymer which will undergo polymerization on a metal surface, such as stainless steel or other steel alloys. The coating formulation forms a thin layer of polymer coating on the surface by chemical grafting involving the use of a graft initiator to create active bonding sites, on the metal surface, for the silicone-based prepolymer to undergo polymerization on the metal surface. Alternatively, the silicone-based prepolymer could include minor amounts of a silane monomer and/or a vinyl monomer, such as a (meth)acrylate monomer. The bonding and polymerization are completed in a single application process without using complex equipment. The coating and process helps surfaces associated with combustion and surfaces subjected to elevated temperature reduce carbon or coke formation at temperatures of about 300 F. up to 700 F. and thereby improves the durability and performance of those surfaces.

The polymerization process is chemical grafting and it requires the activation of a substrate. Once the substrate has been activated, chains of monomers linked by carbon-carbon bonds grow on the substrate as whiskers. These whiskers impart new properties permanently to the substrate without altering any of the existing characteristics of the base materials. Many materials, both natural and synthetic, contain some form of hydrogen that is more reactive than the "bulk hydrogen". As shown in Formula 1 below, the tertiary hydrogen in polypropylene (I), the amide hydrogen in protein (II), and the hydroxyl hydrogen in polysaccharide (III), are some of those examples.

Formula 1

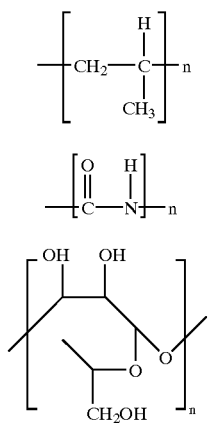

Certain graft-initiators (G.I.) have the capacity of removing these active hydrogens and concomitantly initiating the growth of polymer chains at the site from where the active hydrogen was removed. In the case of polypropylene, this process can be represented in Formula 2. The * represents a free radical, anion or cation, depending on whether the G.I. removes a hydrogen and one electron, no electrons or two electrons, respectively. Because there are a wide variety of monomers, which do not permit the free-radical type of polymerization, it is beneficial to utilize all three hydrogen mechanisms mentioned above to broaden the scope of application for the current invention.

Formula 2

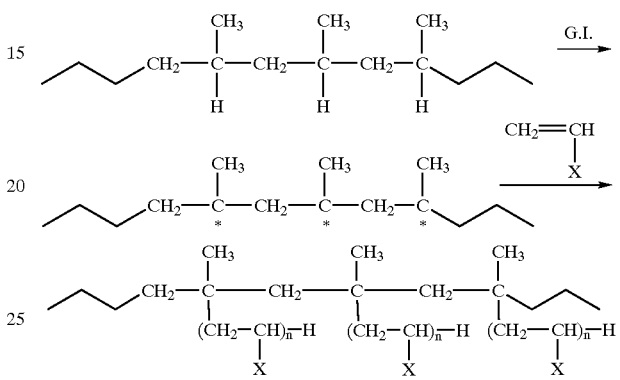

In Formula 2, the vinyl

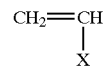

monomer immediately attaches to the activation sites. "X" represents the new property or properties that are imparted. Under certain circumstances, a mixture of monomers could be employed to impart more than one property onto substrate in a single processing step. These polymer chains whose length can be controlled, are permanently attached to the substrate after curing treatment. The linkage between the graft-polymer and the substrate is covalent. Therefore, the grafted vinyl monomers or prepolymers cannot be easily removed from the substrate.

Although the grafting reaction between the metal surface and monomers or prepolymers is thought to involve a reactive species on the steel substrate, the details of the mechanism have not been fully established. In the presence of moisture, there is a layer of oxide and hydroxyl groups tenaciously bound to the steel substrate. The hydrogen of the hydroxyl group may be removed by the graft initiator and form a radical which reacts with the monomer starting graft polymerization. The oxides and hydroxyl groups react with epoxy groups of the prepolymers or monomers initiating a chemical reaction that also leads to a strong bonding between the alloy and organic polymer formed on the surface.

The mechanism of graft polymerization for metal surface may be described in the steps shown in Formula 3. The process of termination may differ when the formulation contains reactive prepolymers or polymers. The prepolymers may also undergo activation by the graft initiator generating reactive radicals P*, which react with the radical on the steel surface forming a graft coating on the substrate.

This process is illustrated in Formula 4.

Formula 3

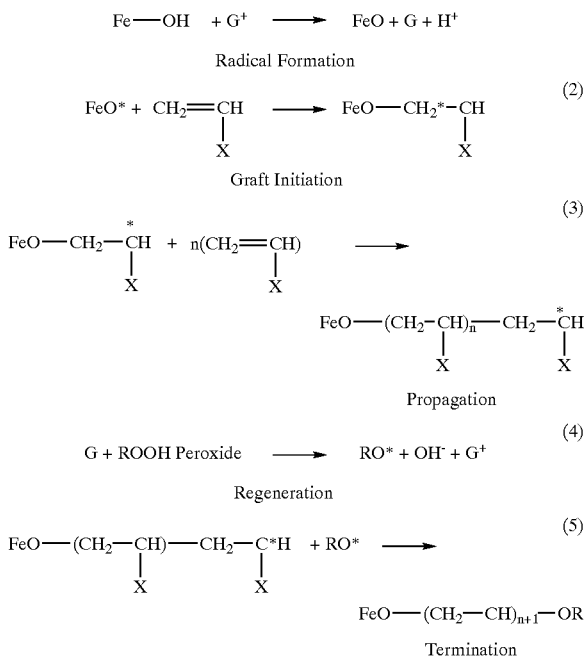

(1) Fe—OH + G$^+$ → FeO + G + H$^+$
Radical Formation (2) FeO* + CH$_2$=CH—X → FeO—CH$_2$*—CH—X
Graft Initiation (3) FeO—CH$_2$—*CH—X + n(CH$_2$=CH—X) →
FeO—(CH$_2$—CH)$_n$—CH$_2$—*CH
          |                    |
          X                    X
Propagation (4) G + ROOH Peroxide → RO* + OH$^-$ + G$^+$
Regeneration (5) FeO—(CH$_2$—CH)—CH$_2$—C*H + RO* →
          |              |
          X              X
FeO—(CH$_2$—CH)$_{n+1}$—OR
Termination Formula 4

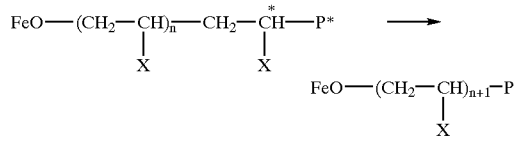

(6) FeO—(CH$_2$—CH)$_n$—CH$_2$—*CH—P* →
          |                    |
          X                    X
FeO—(CH$_2$—CH)$_{n+1}$—P
          |
          X

The graft initiator G may consist of the following metal ions: Fe$^{+++}$, Fe$^{++}$, Ag$^+$, Co$^{++}$, Ni$^{++}$, Ce$^{+++}$ and Cu$^{++}$. The peroxide may be chosen from catalysts such as benzoyl peroxide, methyl ethyl ketone peroxide, tert butyl hydroperoxide and hydrogen peroxide. The monomers and prepolymers have side functional groups X, which may react between themselves and with additional prepolymers or polymers included onto the formulation forming a cross-linked organic coating. The functional groups of the monomers and prepolymers should consist of hydroxyl groups, carbonyl groups, secondary and/or tertiary amino groups and epoxy groups. The molecular ratio of the functional groups of the reactive components are chosen so that no free groups are left after the reaction is completed.

A pre-calculated quantity of silicone prepolymer Silikophen 80/20 was prepared in a container. Then, the other ingredients were added in the proper ratio and sequence as described in the sample formulations. The contents were stirred to a uniform solution. The concentration of the ingredients was measured by weight. Examples of the formulations are presented in Table I.

TABLE I

| Item | Description of Ingredient | Example 1 (Grams) | Example 2 (Grams) | Example 3 (Grams) | Example 4 (Grams) |
|---|---|---|---|---|---|
| 1 | Silikophen P80/20 Silicone Prepolymer | 600 | 100 | 100 | 72 |
| 2 | GE SR125 Silicone Prepolymer | 600 | 900 | — | — |
| 3 | GE SR112 Silicone Prepolymer | — | — | 900 | 840 |
| 4 | Methyl Ethyl Ketone Solvent | 600 | 600 | 600 | 544 |
| 5 | Xylene Solvent | 540 | 400 | 400 | 368 |
| 6 | Cellosolve Acetate Solvent | 500 | 300 | 300 | 280 |
| 7 | Bentone SD2 Additive | 10 | 10 | 10 | 6 |
| 8 | Troymax 8% Zinc | 2 | 4 | 4 | 4 |
| 9 | A1100 Silane Monomer | 0.1 | 0.1 | 0.1 | 0.1 |
| 10 | Hexafluoro Butyl Methacrylate Monomer | 0.01 | 0.01 | — | — |
| 11 | Trifluoro Ethyl Methacrylate Monomer | — | 0.1 | 0.01 | 0.01 |
| 12 | Benzoyl Peroxide Graft Initiator | 0.001 | 0.001 | 0.001 | 0.001 |

TABLE II

Ingredients

| Ingredient | Manufacturer |
|---|---|
| Silikophen P80/20 Silicone Prepolymer is a Polysiloxane Resin | Goldschmidt Chemical Corporation |
| GE SR125 Silicone Prepolymer is a methylphenylpolysiloxane solution | GE Silicones |
| GE SR112 Silicone Prepolymer is a methylphenylpolysiloxane solution | GE Silicones |
| Methyl Ethyl Ketone Solvent | Shell Oil Company |
| Xylene Solvent is an aromatic hydrocarbon solvent | CITGO Petroleum Corporation |
| Cellosolve Acetate Solvent is a propylene glycol monomethyl ether acetate | Eastman Chemical Company |
| Bentone SD2 Additive is a rheological additive | Rheox Inc. |
| Troymax 8% Zinc is a Zinc Alkanoate Catalyst | Troy Chemical |
| Silane Monomer A1100 is a gamma-Aminopropyltriethoxysilane | Witco Corporation |
| Hexafluro Butyl Methacrylate Monomer | Aldrich Chemical |
| Trifluoro Ethyl Methacrylate Monomer is a 2,2,2-Trifluoroethyl 2-Propenoic Acid Ester | Monomer-Polymer and Dajac Laboratories, Inc. |
| Benzoyl Peroxide Graft Initiator | Dajac Laboratories, Inc. |

The coating formulation can be applied onto the metal surface in a number of different ways. It is important that the surface to which the coating will be applied be as clean as possible. It should have no grease or oil on the surface which could interfere with the chemical grafting. Preferably it is applied by having all the ingredients mixed together. For example, the polysiloxane polymer can be applied to the surface as a liquid formulation containing a mixture of polysiloxane or silicone prepolymer, a silane monomer, a vinyl monomer such as a (meth)acrylate monomer, a graft initiator, a catalyst, a solvent, and additives. Further, other polysiloxane prepolymers could be employed such as GE SR 940 silicones or Dow Corning 804 silicones. The additives could include those compositions normally added to coating compositions to adjust their performance or control the rheology of the coating formulation, such as thickeners, fillers, leveling agents, wetting agents, defoamers, and the like. There is no criticality in the selection neither of the solvent employed or in the combination of solvents or the ratio of the solvents when used as a combination of solvents. Typically, a combination of solvents proves to be the most effective, but the coating should work with a single solvent. The polymer coating is about 0.0005 to about 0.003 inch thick. Convenient methods for applying the coating composition are dipping, spraying and pumping. For inside walls of the fuel injector, coating solution is forced through the passages by a MasterFlex liquid pump. In order to drain the excessive formulation, the injector passage needs to be purged by compressed air.

The coated injector was then cured in the oven at 100° C. for 30 minutes followed by a final cure at 225° C. for one hour. After one and one-half hour in the oven, the injector is removed allowing it to cool down to ambient temperature. The curing conditions are not critical, although the two step cure is preferred. The precise conditions will depend upon the prepolymers and/or monomers employed, but it is expected that the curing will be done at a temperature range of about 85° C. to about 300° C., with a range of about 100° C. to about 225° C. being preferred, for a period of about 1 to about 3 hours duration.

In order to demonstrate the utility of the coatings in accordance with the present invention, a laboratory test rig, which is shown in FIG. 1, was set up to conduct an evaluation of coating compositions Example 1 and 2, which are set forth in Table I. It was devised to simulate the typical fuel flow conditions inside fuel injectors using straight tubes. The test tube is shown in cross-section in FIG. 2.

The test tube 1 has a straight center section 2, enlarged end sections 3 and 4 to facilitate placement in a heated copper cylinder 10, and connections to lines feeding fuel into and out of the test tube. The enlarged ends 3 and 4 comprise openings 5 and 6 for connecting to the inlet and outlet lines, and a transitional section 7 and 8 which are in communication with the central heated region 2 of the test tube 9. The copper cylinder 10, for the purpose of the test, comprised a central section 9 having a thickness of 0.25" and end sections having a thickness of 1.0". The center section of the cylinder 9 had a hole with a diameter of 0.0625".

As seen in FIG. 1, the tube 1 is inserted into the copper cylinder 10, which is wrapped around by the band heater 11, the band heater is in turn surrounded by insulation 12. Fuel is fed to the test setup from a fuel supply tank 13. The fuel is pumped by a pump 14. To insure that particulate matter does not reach the test cylinder, fuel filters 15 and 16 are placed ahead of and after the fuel pump 14. To facilitate an even flow of fuel, an accumulator 17 is placed in the fuel line. To control the fuel temperature, the fuel passes through a fuel pre-heater 18 before entering the test tube via line 19. A temperature controller 20 is employed to set the fuel and tube wall temperatures. The fuel, after passing through the test tube 1, exits via line 21 and passes through a heat exchanger 22 to reduce the temperature of the exit fuel, which passes to waste tank 23. Pressure gauge 24 and pressure regulator 25 are used to regulate the line pressure to prevent two-phase flow from occurring.

Figure 2:
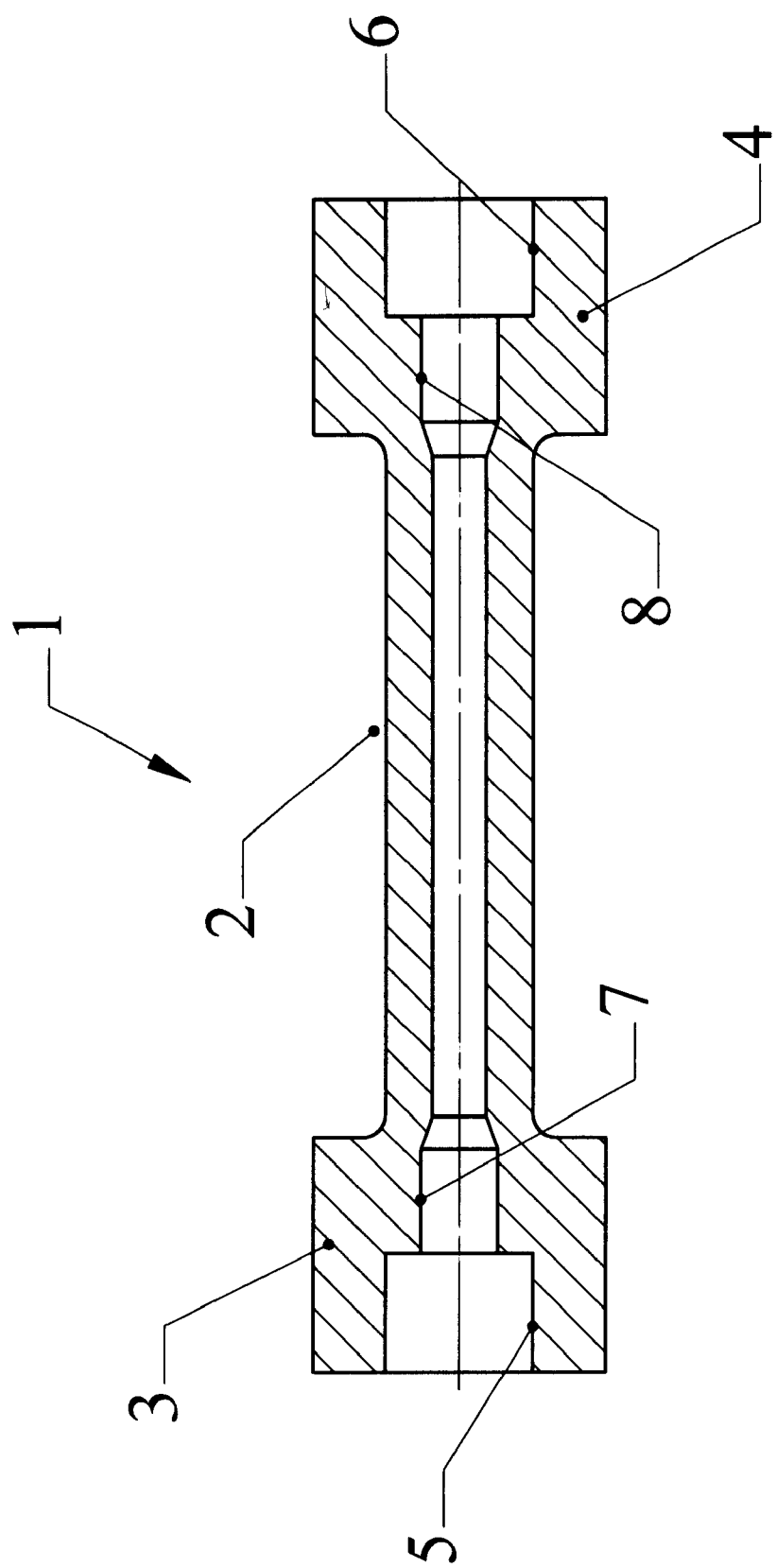
FIG. 2 is a cross-sectional view of the test tube.

Only the central 0.300-inch section of the test tube 1, as shown in FIG. 2, is directly in contact with the heating cylinder 10. Three thermocouples (not shown) were embedded between the cylinder 10 and the exterior of the tube surface 1 for monitoring and controlling of the wall temperature. The wall temperature was set at 600° F., and the fuel volume flow rate was maintained at 20 cc/min. The fuel inlet temperature was in the 320 to 350° range. Jet-A fuel was used in all of the tests, and it was not recirculated through the apparatus.

After each test, the test tube was sliced in half along its axis to expose the interior wall surface, allowing a detailed analysis of the deposits. Quantitative deposit analyses were conducted using an Elemental Analyzer to measure the amount of deposits. Visual and photographic methods were also used to provide a qualitative comparison of the coating performance and deposit results. The coatings in Examples 1 and 2 were applied to four different stainless steel materials, namely 316ss, 410ss, 440Css, and 17-4PH.

All the tests were conducted using a wall temperature of 600° F., a fuel flow rate of 20 cc/min, a fuel inlet temperature of 320° F., and a test duration of 40 hours. The surface finish of the tubes was estimated to be 32 micro-inches. The test results summarized in Table III show that the coating of Example 2 resulted in better performance with no deposits.

TABLE III

| Test No. | Material Type | Coating Example No. | Visual Result |
|---|---|---|---|
| 1 | 440C | None | Heavy deposits |
| 2 | 410 | None | Medium deposits |
| 3 | 316 | None | No deposits |
| 4 | 316 | 2 | No deposits |
| 5 | 440C | 1 | Little to no deposits |
| 6 | 440C | 2 | Little to no deposits |
| 7 | 410 | 1 | Heavy deposits |
| 8 | 410 | 2 | No deposits |
| 9 | 17-4PH | 1 | No deposits |
| 10 | 440C | 2 | No deposits |
| 11 | 410 | 2 | No deposits |

Additional tests were made using the composition of Example 2 on a variety of additional compositions, including 410ss, IN625, IN718, HAST-X, 347ss, 17-4PH, 440Css, 440Fss and Greek Ascoloy, and the results are shown in Table IV. The surface finish on the tubes was estimated to be 200 micro-inches. The tests were conducted using a fuel flow of 20 cc/min, a wall temperature of 600° F., fuel inlet temperatures of 350° F., and a test duration of 40 hours. The results summarized in Table IV indicate that the nickel-based alloys appear to be more compatible with the present formulations and showed the most reduction in carbon formation. Further, the results in Table IV show that, at a higher fuel inlet temperature and a coarser surface finish, the coating of the present invention provides greater protection against coking as compared to uncoated surfaces. The results also show that, while no single formulation is compatible for all the stainless steel alloys and that the chemical composition of the alloys has a strong influence on the effectiveness of the coating, the composition of the present invention significantly reduces carbon build-up. As noted, the surface finish or texture of the substrate appears to play an important role in determining the results of the coating formulation. Generally, the finer the surface finish, the better the coating performance. Thus, it is desirable that the surface finish be maintained at no more than 300 micro-inches, preferably less, with no more than 32 micro-inches being preferred.

Table IV

| Test No. | Material Type | Coating Example No. | Test Result |
|---|---|---|---|
| 12 | 316 | 2 | Medium Deposits |
| 13 | HAST-X | 2 | Light deposits |
| 14 | 347 | 2 | Light deposits |
| 15 | 440C | 2 | Medium deposits |
| 16 | 410 | 2 | No deposits |
| 17 | 17-4PH | 2 | Light deposits |
| 18 | 440F | 2 | Heavy deposits |
| 19 | IN625 | 2 | No deposits |
| 20 | IN718 | 2 | No deposits |
| 21 | GR-ASC | 2 | Medium deposits |
| 22 | 316 | None | Heavy deposits |
| 23 | 440C | None | Heavy deposits |
| 24 | 410 | None | Heavy deposits |

Figure 3:
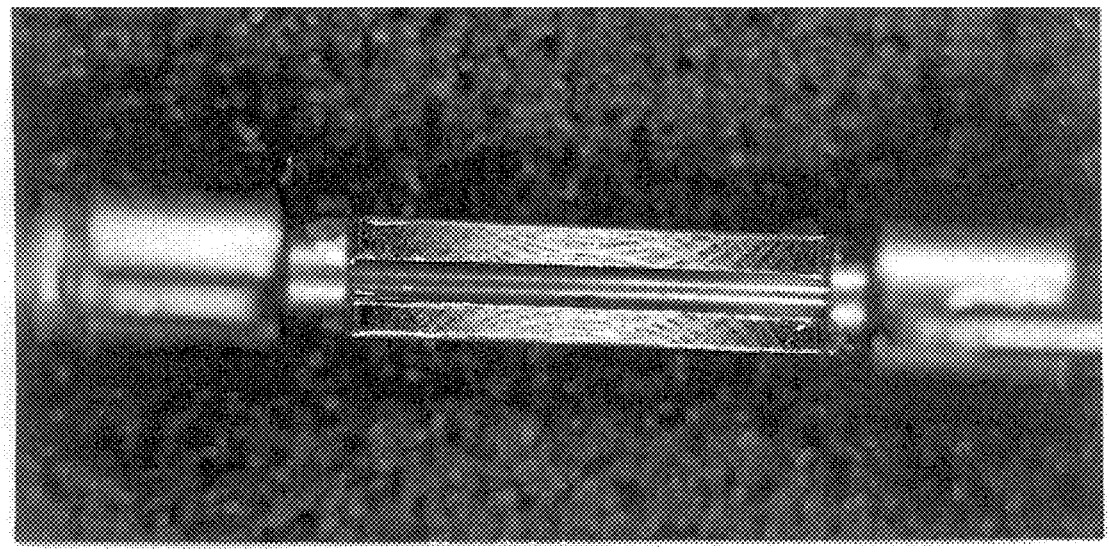
FIG. 3 is a photographic comparison between an uncoated sample tube (FIG. 3A) and a coated sample tube (FIG. 3B), both of which were tested at a wall temperature of 600° F.
Figure 3:
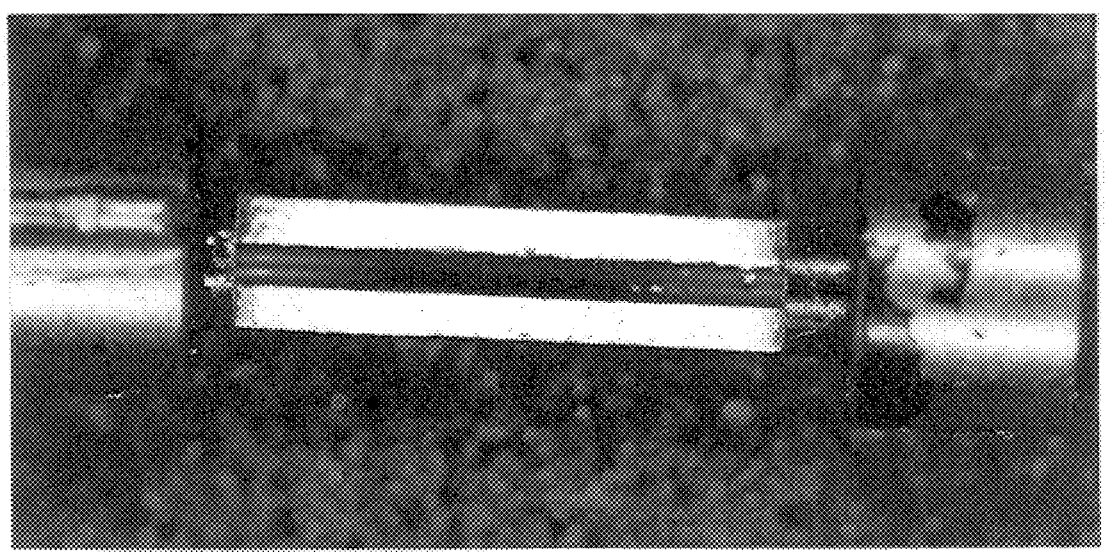

Photograph FIG. 3 shows a comparison of carbon formation between an uncoated 410ss sample tube and a tube coated with the composition of Example 2. This is a visual of the test result comparing an uncoated 410 stainless steel tube (Test 2) against a 410 stainless steel tube coated with the composition of Example 2 (Test 11). As can be seen in the photos in FIG. 3, the uncoated sample tube resulted in significant deposits of carbon, while the coated tube shows no deposits of carbon. The interior wall of the coated tube only exhibits a slight change of color due to heating.

The coating compositions of Examples 3 and 4 also were evaluated by applying them to the inside of tubes, similar to those describe in the tests involving Examples 1 and 2. The coated tubes were then evaluated against an uncoated tube by flushing the inside of the tube with fuel and then putting the tube in a test oven for thirty minutes at 400° F. This was repeated, i.e., the flushing and heating in a oven cycle, for about 80 hours. After that, the tube was sliced in half and visually inspected. Carbon was found to have built up on the uncoated tube, while none was found on the coated tubes, although the coating showed a slight change in coloring due to the heating.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

I claim:

1. A deposit-resistant fuel-supply or injection component, comprising said component having a coating on at least one surface thereof to prevent carbon or coke formation at high temperatures, said coating comprising a polysiloxane polymer which is applied to the surface as a solution and is graft polymerized to the surface of the component to thereby resist deposit of carbon or coke.

2. The component of claim 1 wherein the polysiloxane polymer is a methylphenylpolysiloxane polymer.

3. The component of claim 1 wherein the polysiloxane polymer is applied to the surface as a solution of a polysiloxane prepolymer, a silane monomer and a vinyl monomer.

4. The component of claim 3 wherein the vinyl monomer is selected from the group consisting of hexafluoro butyl methacrylate monomer and trifluoro ethyl methacrylate monomer.

5. The component of claim 1 wherein the polysiloxane polymer is applied to the surface as a liquid formulation containing a mixture of siloxane prepolymer, a graft initiator, and a catalyst.

6. The component of claim 1 wherein the surface is a stainless steel or a stainless steel alloy.

7. The component of claim 1 wherein the coating is effective at temperatures from about 300° F. to about 700° F.

8. The component of claim 1 wherein the polymer coating is about 0.0005 to about 0.003 inch thick.

9. The component of claim 1 wherein the graft polymerization is initiated by a metal ion selected from the group consisting of $Fe^{+++}$, $Fe^{++}$, $Ag^+$, $Co^{++}$, $Ni^{++}$, $Ce^{+++}$, and $Cu^{++}$.

10. The component of claim 1 wherein the polysiloxane polymer is applied to the surface as a liquid formulation containing a mixture of siloxane prepolymer, a silane, a vinyl monomer, a graft initiator, a catalyst, a solvent, and additives.

11. The component of claim 1 wherein said polysiloxane polymer is obtained by polymerizing a polysiloxane prepolymer with minor amounts of a silane monomer and a vinyl monomer.

* * * * *